United States Patent [19]
Zombo et al.

[11] Patent Number: 5,442,285
[45] Date of Patent: Aug. 15, 1995

[54] NDE EDDY CURRENT SENSOR FOR VERY HIGH SCAN RATE APPLICATIONS IN AN OPERATING COMBUSTION TURBINE

[75] Inventors: Paul J. Zombo, Cocoa, Fla.; Michael J. Metala, Murrysville, Pa.; Charles C. Moore, Hibbs, Pa.; Paul Guenther, Murrysville, Pa.; Oran L. Bertsch, Titusville, Fla.

[73] Assignee: Westinghouse Electric Corporation, Pittsburgh, Pa.

[21] Appl. No.: 203,466

[22] Filed: Feb. 28, 1994

[51] Int. Cl.⁶ .................. G01N 27/90; G01H 11/02
[52] U.S. Cl. ................................ 324/227; 73/660; 324/207.18; 324/219; 324/226; 324/240; 324/241
[58] Field of Search .......... 324/207.16–207.19, 324/219, 225, 226, 227, 232, 238–243; 73/658–661; 340/679, 683

[56] References Cited

U.S. PATENT DOCUMENTS

| | | | |
|---|---|---|---|
| 3,528,003 | 9/1970 | Forster | 324/227 |
| 3,750,010 | 7/1973 | Abnett et al. | 324/225 |
| 3,854,085 | 12/1974 | Mansson et al. | 324/227 |
| 4,430,614 | 2/1984 | Gereg | 324/238 |
| 4,518,917 | 5/1985 | Oates et al. | 324/225 X |
| 4,839,592 | 6/1989 | Vitulli, Jr. | 324/227 |
| 4,853,634 | 8/1989 | Tornblom | 324/227 X |
| 4,954,777 | 9/1990 | Klopfer et al. | 324/227 X |

OTHER PUBLICATIONS

CRC Press; *The Electrical Engineering Handbook;* pp. 35–36, 1019, 1024.
American Society for Metals; *Metals Handbook, 8th Edition, vol. 11, Nondestructive Inspection and Quality Control;* "Eddy-Current Inspection"; pp. 75–87.

*Primary Examiner*—Gerard R. Strecker
*Attorney, Agent, or Firm*—M. G. Panian

[57] ABSTRACT

The present invention provides an eddy current sensing device capable of in-situ operation within a high temperature and high vibration environment of a combustion turbine engine. The eddy current sensing device is preferably utilized in an eddy current sensing system for monitoring crack formation and displacement of rotating members of the combustion turbine engine. The method according to the present invention provides inducing eddy currents in the rotating member, detecting the eddy currents, providing a signal indicative of the detected eddy currents, filtering the signal based on the condition to be monitored and evaluating the filtered signal to determine whether the condition, such as the formation of a crack in the surface of the rotating member exists, and if so, determining whether the condition is critical or routine.

14 Claims, 7 Drawing Sheets

NDE EDDY CURRENT SENSOR FOR VERY HIGH SCAN RATE APPLICATIONS IN AN OPERATING COMBUSTION TURBINE

FIELD OF THE INVENTION

The present invention relates to an eddy current sensing system for monitoring a rotating member for various conditions. More particularly, the eddy current sensing system of the present invention monitors the formation of surface defects and displacement of rotating members within an operating combustion turbine engine.

BACKGROUND OF THE INVENTION

The use of eddy current sensors has been found to be effective for detecting various physical, structural and metallurgical conditions in a wide variety of materials. In particular, eddy current sensors have been used in diverse applications to inspect manufactured parts.

Eddy current inspection is based on principles of electromagnetic induction. Therefore, eddy current inspection techniques are non-contact techniques in that they do not require direct electrical contact with the material or part to be inspected. Moreover, eddy current sensors are non destructive in that they do not require destruction of the part to be analyzed.

Typically, an object to be inspected is placed within or adjacent to an electrical coil in which an alternating current is flowing. As a result of the alternating current known as the driving current, eddy currents are caused to flow in the object due to electromagnetic induction. Since eddy currents oppose the primary induction current, their effects can be measured. When a crack or other defect is present on or near the object's surface, the eddy current flow is affected, which in turn causes changes in the associated electromagnetic field. The effect of the electromagnetic field can then be monitored or sensed by observing the induced voltage in one or more other coils placed within the electromagnetic field near the object's surface.

Unfortunately, currently available eddy current sensors are incapable of withstanding an aggressive environment such as one within an operational combustion turbine engine. In fact, currently available eddy current sensors are only operational up to approximately 165° C. (330° F.). The environment inside an operating combustion turbine engine generally varies from temperatures in excess of 165° C. (330° F.) to temperatures of approximately 1204° C. (2200° F.) depending upon the location within the turbine.

Conventional eddy current sensors are commercially available for inspecting a number of conditions in various materials or metal parts. For instance, it is desirable to monitor rotating parts of a combustion turbine engine to detect various conditions such as crack formation and displacement so that the turbine may be shut down safely, thereby avoiding further damage. However, conventional eddy current sensors are limited by their design so that they are incapable of providing a scan rate in excess of approximately 127 meters/sec. (5000 inches per second). If real time monitoring is desired for parts in a machine such as an operational combustion turbine it should be appreciated that higher scan rates are required.

Therefore, there is a need for a high resolution eddy current sensor capable of withstanding an aggressive environment which can be used in an eddy current sensing system to monitor various condition using a high scan rate so that real time monitoring can be achieved.

SUMMARY OF THE INVENTION

It is, therefore, an object of the present invention to fulfill this need by providing both a high resolution eddy current sensor specifically designed to operate within an aggressive environment in terms of temperature and vibration and an eddy current sensing system to monitor various conditions in real-time.

The eddy current sensor according to the present invention comprises a driver coil for inducing an eddy current in a rotating member, at least one pickup coil for detecting the induced eddy current, and a cylindrical core around which the driver and pickup coils form concentric rings of coils. In a preferred embodiment, the cylindrical core is hollow so that cool air may be pumped into the hollow portion thereby cooling the driver and pickup coils so that they may be utilized in a high temperature environment. It is also preferred that two pickup coils be used and that they be coupled together differentially.

In a more preferable embodiment, the eddy current sensor also comprises a housing surrounding the concentric rings of coils, coil potting material to position the coils, and a coil shield partially surrounding the concentric rings of coils to define a window through which electromagnetic induction and detection is possible.

A combination of the driver and pickup coils is defined as a coil sensor. In an embodiment in which it is desired to monitor the progression of a defect, two or more coil sensors are positioned in series along the cylindrical core.

An eddy current sensing system preferably comprises the eddy current sensor according to the present invention for detecting the eddy currents induced in a rotating member and providing an output indicative of the detected eddy currents, an eddy current testing instrument for filtering the sensor output based on various conditions of the rotating member which are to be monitored, and a diagnostic system for evaluating the filtered outputs to determine at least whether a condition exists. The diagnostic system comprises a threshold detector which determines that a condition exists when the filtered output exceeds a predetermined threshold and an assessment means which, when the filtered output exceeds the predetermined threshold, analyzes the filtered output to determine whether the condition is routine or critical.

In a preferred embodiment, the eddy current sensing system is used to monitor defects in the surface of a rotating member of a combustion turbine engine and a displacement of a rotating member of a combustion turbine engine. In a more preferred embodiment, the eddy current sensing system is capable of monitoring the progression of the monitored conditions.

An in-situ method is also provided by the present invention in which various conditions of a rotating member are monitored by the eddy current sensing system. The method provides for inducing an eddy current in the rotating member, then detecting the induced eddy current, providing a signal indicative of the detected change in eddy current, filtering the detected signal to produce a filtered signal indicative of the conditions to be monitored, identifying occurrences in which the filtered signal exceeds a predetermined threshold, and analyzing the filtered signal to determine whether a condition exists. In a preferred embodiment, the method further provides for determining whether an existing condition is critical or routine. If the condition is critical a shut down procedure is automatically initiated and an alarm is triggered in a remote diagnostic center.

BRIEF DESCRIPTION OF THE DRAWINGS

The present invention will be better understood, and its numerous objects and advantages will become apparent by reference to the following detailed description of the invention when taken in conjunction with the following drawings, in which.

DETAILED DESCRIPTION OF THE PREFERRED EMBODIMENT

Figure 1:
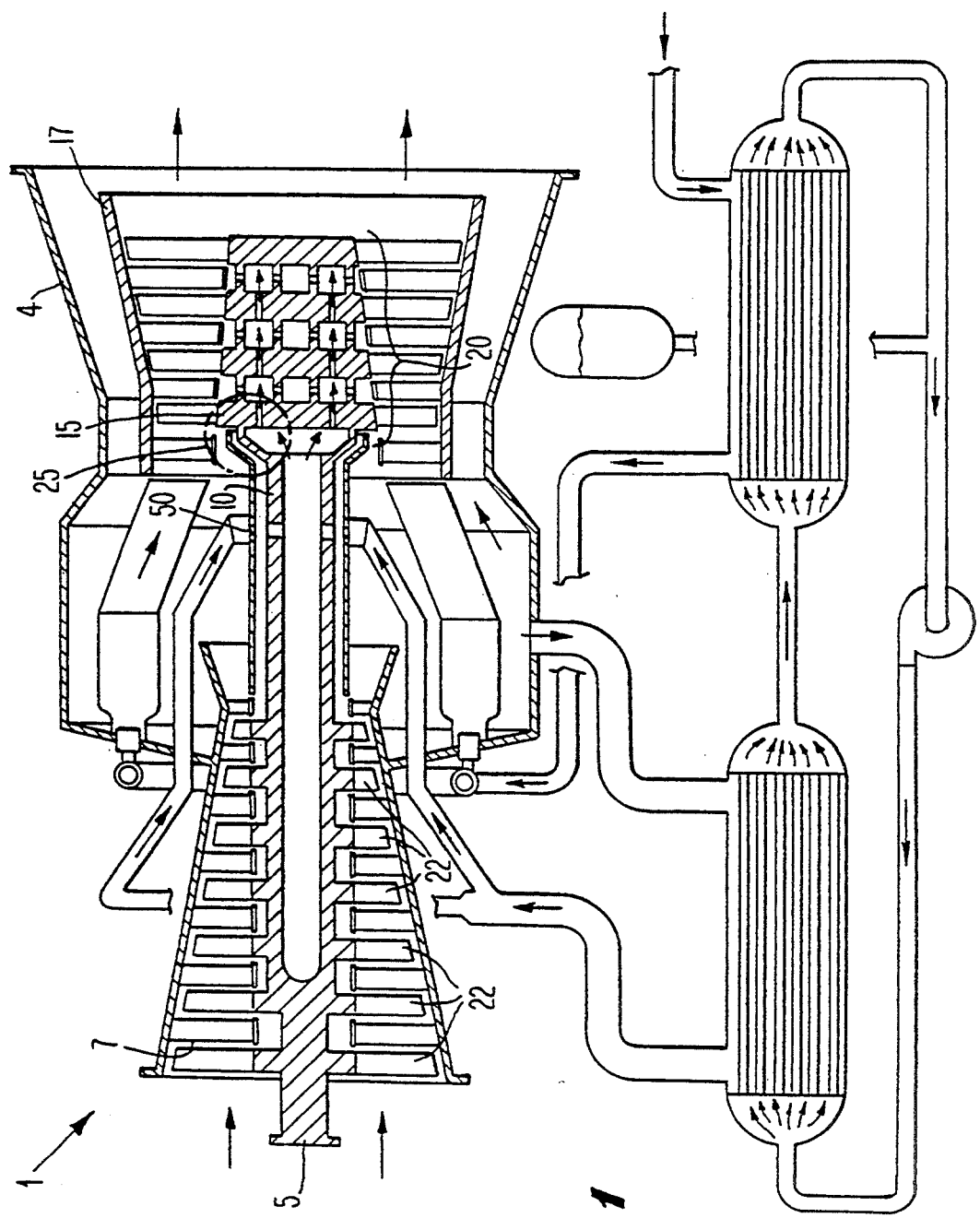
FIG. 1 is a cross sectional diagram of a combustion turbine engine in which a preferred embodiment of the invention may be used.

Although the present invention may be utilized in a wide variety of applications, it will be described herein as applied to monitoring conditions in rotating members of a combustion turbine engine. However, it should be understood that the present invention is not so limited. A combustion turbine engine is shown generally at 1 in FIG. 1. The combustion turbine engine's central axis is shown as rotor 5 which rotates at approximately 3600 rpm when the combustion turbine engine is fully operational. Thus, the compressor blades 22, compressor discs 20, air separator 10 and other members all fixed to rotor 5, likewise rotate at about 3600 rpm. It is often desirable to detect crack formation on the portion of the air separator 10 which extends radially outward towards the row 1 disc 15 as shown by the circled portion designated as 25 in FIG. 1.

Figure 2:
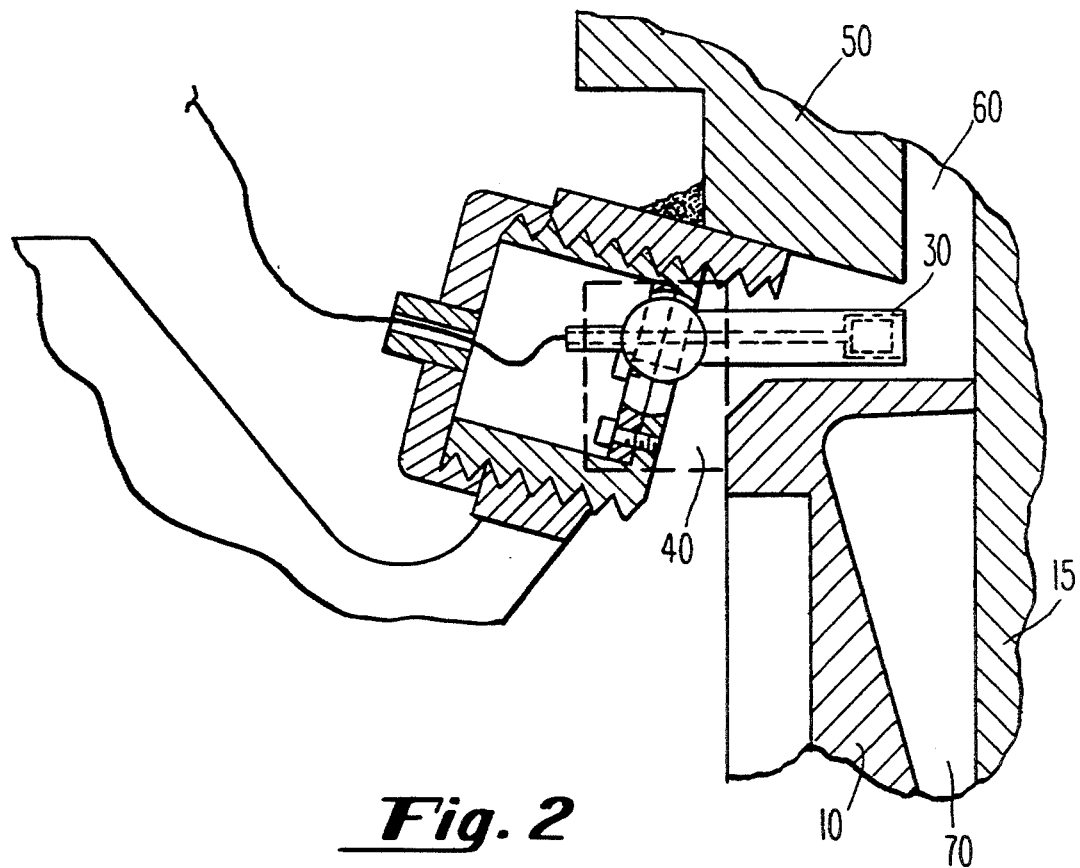
FIG. 2 is a magnified cross sectional view of the portion of the combustion turbine engine shown in FIG. 1 in which a preferred embodiment of the present invention may be used.

FIG. 2 provides a magnified view of the air separator 10 and the row 1 disc 15. An eddy current sensor is shown generally at 30 in FIG. 2 disposed above the rotating portion of air separator 10. The eddy current sensor can be mounted on the engine's torque tube housing 50 preferably using a support positioning device 40.

It should be understood that the support positioning device 40 can be implemented using any suitable connecting device.

Figure 3A:
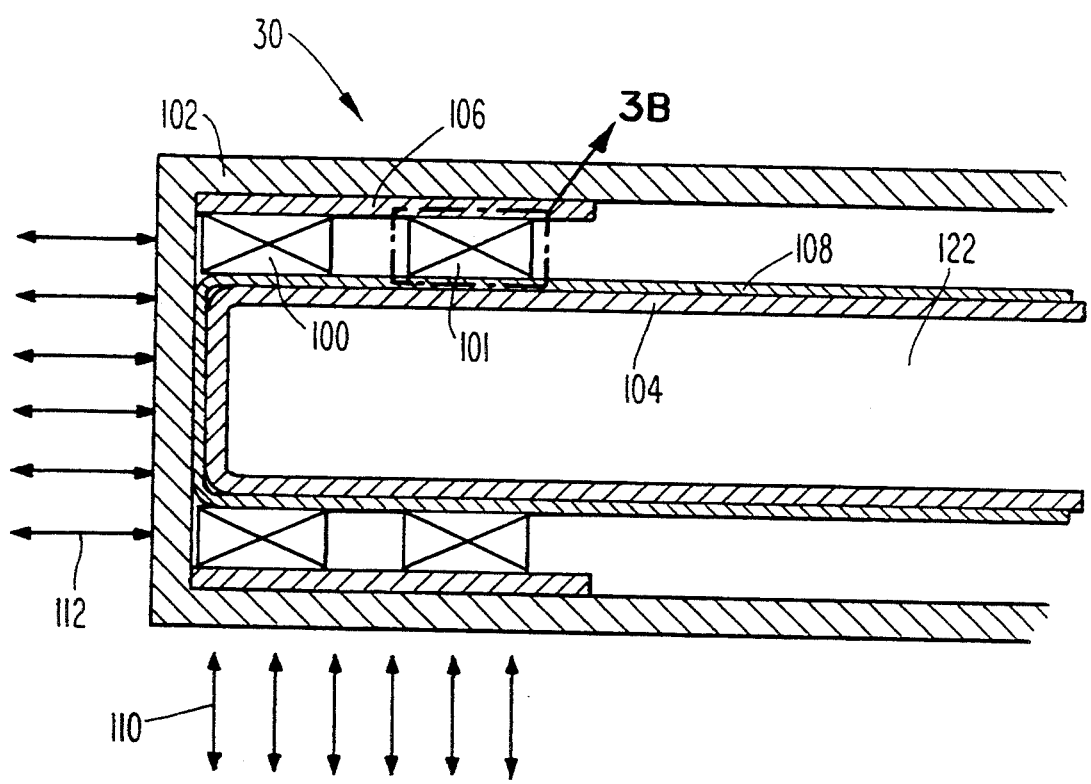
FIG. 3A and 3B are axial cross sectional diagrams of the eddy current sensor according to a preferred embodiment of the present invention.
Figure 3B:
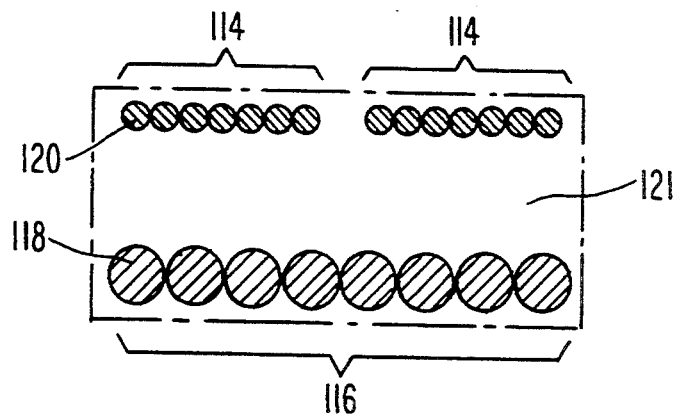

An axial cross sectional view of an eddy current sensor according to a preferred embodiment of the present invention is shown in FIGS. 3A and 3B. A coil sensor 100 includes a driver coil 116 and preferably two pickup coils 114 which are coupled together differentially as shown in FIG. 3B. The wires of each of the coils are threaded around the sensor's cylindrical core 108 such that the sensor coil 100 forms a donut shape. Cross sections of the driver coil wire 118 and cross sections of the pickup coil wire 120 are shown in FIG. 3B illustrating the threaded cross sectional view and orientation of the coils. A sensor housing 102 is shown to encompass the sensor coil 100. A coil shield 106 may optionally be provided to direct the electromagnetic field produced by the driver coil. The details of the coil shield 106 will be described below.

Referring back to FIG. 2, the temperature of the air in interstice 70 while the turbine is operational, is approximately 190° C. (375° F.), and the temperature of the air above air separator 10 is approximately 218° C. (425° F.), well above the operating temperatures for commercially available eddy current sensors. Thus, the design and material used in manufacturing the eddy current sensor shown in FIGS. 3A and 3B must be carefully selected to achieve operability in this high temperature environment. It is therefore, preferable that high temperature materials be used to construct the eddy current sensor. To achieve operability at even higher temperatures, it is additionally preferable to provide a cylindrical core 108 which has a hollow portion 122 in which adequately cooler air is pumped thereby further cooling the coil sensor 100.

A ceramic insulator 104 may also be used to coat the inner surface of cylindrical core 108. The coil sensor 100 preferably contains potting material 121 to position the driver coil 116 and pickup coils 118. Suitable high temperature potting material is commercially available from GK Engineering, Inc. of Chatsworth, California. In such a preferred embodiment, the thermal expansion coefficient of the potting material should be greater than the thermal expansion coefficient of the housing 102. Still further, it is preferable to use specially insulated wire for both the driver coil 116 and the pickup coil 118 for use in high temperature applications. A ceramic coated wire is especially preferred for use in operational environments having temperatures above 165° C. (330° F.). Wire coated with a high temperature ceramic coating is commercially available from California Fine Wire, Inc. It should be understood that although ceramic coated wire can be used at temperatures up to 1093° C. (2000° F.), other coated wire may be used at lower temperatures, e.g., polyamide coating for applications up to about 215° C. (420° F.).

The material selected for the sensor housing may also be selected based upon the high temperature and hydrostatic load conditions which exist in the operating combustion turbine engine. For instance, the thermal expansion characteristics, conductivity, and permeability should all be considered in the selection of an appropriate material for the sensor housing. Preferably, the sensor housing 102 is made of a nickel based alloy such as IN 909 commercially available from Inconnel or an equivalent thereof having a lower thermal expansion coefficient than the potting material, a permeability of 1.0 and a conductivity of less than 3% IACS (International Annealed Copper Standard). More preferably, the sensor housing material has a conductivity less than 1.5% IACS. Notwithstanding a selection of material as described herein, cool air is preferably pumped into the hollow portion 122 of the sensor for operational temperatures over 815° C. (1500° F.).

As indicated by FIG. 3B, it is preferable that the driver coil wire 118 be larger in diameter and located closer to the cylindrical core 108 than the pickup coil wire 120. To achieve the best trade off between depth penetration and sensitivity, the size of each coil must be carefully selected depending upon the particular application. It should be understood that larger gauge wire can carry a current with a greater magnitude than a lower gauge wire such that the electromagnetic field produced by the larger gauge wire will be larger and can induce eddy currents at a greater distance. However, it should also be understood that lower gauge wire is desirable to achieve greater sensitivity in sensing the electromagnetic fields produced by the induced eddy currents. Therefore, it is preferable to use 20–30 gauge wire for the driver coil 116 and 26–40 gauge wire for the pickup coils 114 for monitoring surface defects in a rotating member of a combustion turbine engine.

Figure 4:
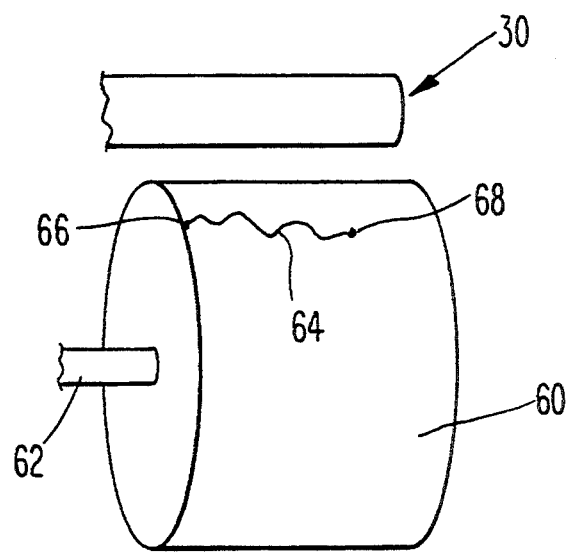
FIG. 4 shows the disposition of the eddy current sensor for monitoring the formation of a crack on the surface of a rotating member.

In a combustion turbine engine, it is known that cracks form on the surface of a rotating member and that each crack generally progresses in the same direction. Referring to FIG. 4, the eddy current sensor 30 is shown positioned above a rotating member 60. The rotating member 60 rotates about an axis 62. It is known, for instance, that a crack 64 will form from a point 66 and progress across the surface of rotating member 60 towards point 68. If two differential pickup coils are used in the coil sensor then their combined output will remain a "0" level as long as no cracks (or other detectable anomalies) exist on the surface of the rotating member 60. But once a crack forms, it can be detected because the output of the differential pickup coils will be non-zero. If it is desired to track the progression of a crack forming on the surface of the rotating member, the eddy current sensor preferably includes a number of coil sensors, such as coil sensors 100 and 101, positioned serially along the axis of the cylindrical core 108 as shown in FIG. 3A. Therefore, as the crack progresses, it is detected by the first coil sensor 100 at a first position and subsequently detected by the second coil sensor 101 at a second position, and so on for each coil sensor used.

Another advantage of the eddy current sensor according to the design of the present invention is that it may simultaneously be used to monitor more than one condition. For instance, by referring back to FIG. 2, it can be seen that the eddy current sensor is not only disposed above the rotating surface of the air separator 10, but it is also disposed adjacent to the radial surface of the row 1 disc 15. Therefore, the eddy current sensor is also capable of detecting displacement of the first disc 15 caused by the high vibration of an operating combustion turbine. Thus, the eddy current sensor shown in FIG. 3A is shown as inducing and detecting electromagnetic fields 110 to monitor the formation of a crack in the surface of a rotating member and additionally, inducing and detecting electromagnetic fields 112 to monitor the displacement of a rotating member.

Figure 5A:
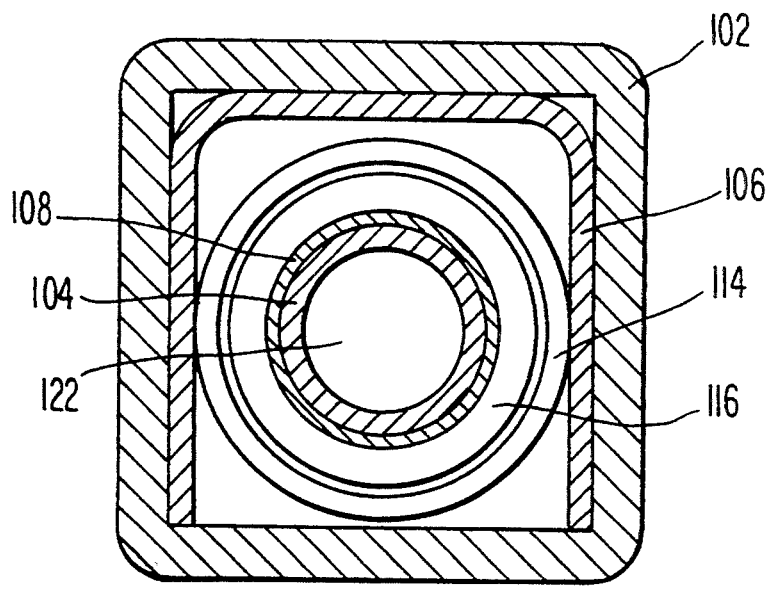
FIG. 5A shows a U-shaped coil shield configuration of an eddy current sensor according to one embodiment of the present invention.
Figure 5B:
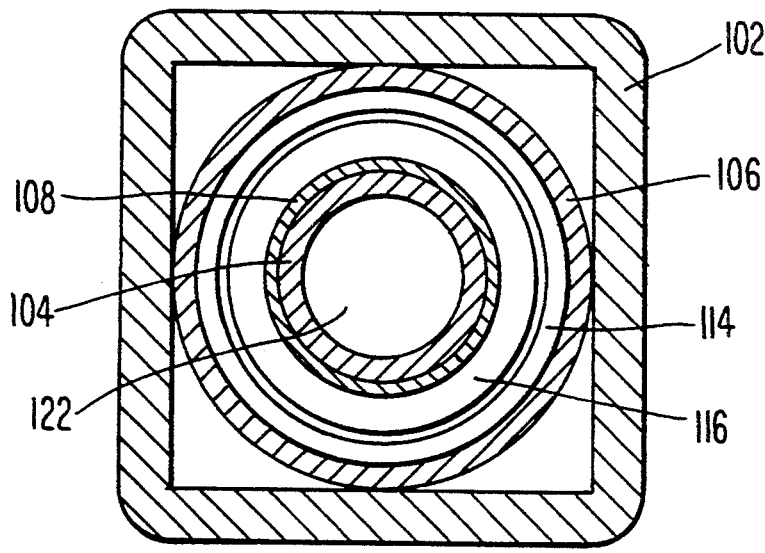
FIG. 5B shows a cylindrical coil shield configuration according to another embodiment of the present invention.

FIGS. 5A and 5B demonstrate two optional uses for a coil shield. In some situations it may be desired to limit the electromagnetic induction field. Thus, the coil shield 106 is preferably made from a ferromagnetic material so that the electromagnetic fields do not penetrate outside of the shield and onto adjacent objects. For instance, if the eddy current sensor can be positioned in a combustion turbine engine as shown in FIG. 2, it may be used to monitor the air separator 10 or the row 1 disc 15, or both. As an example, the coil shield 106 shown in FIG. 5B encircles the entire coil sensor 100 thereby limiting the induction field to be emitted solely from the radial face of the coil sensor so that only a displacement of the row 1 disc 15 is monitored.

Further it is often desirable to limit the induction field window to improve sensitivity of the sensor, i.e. the energy becomes more concentrated thereby improving sensitivity. The U-shaped coil shield 106 shown in FIG. 5A is an example of a coil shield sensor for limiting the induction field window to improve the sensor's overall sensitivity. However, it should be understood that by limiting the window to improve sensitivity there exists a trade off in scanning coverage. Thus, numerous coil shield arrangements are possible but should be selected to maximize the trade off between sensitivity and coverage for each application.

Figure 6:
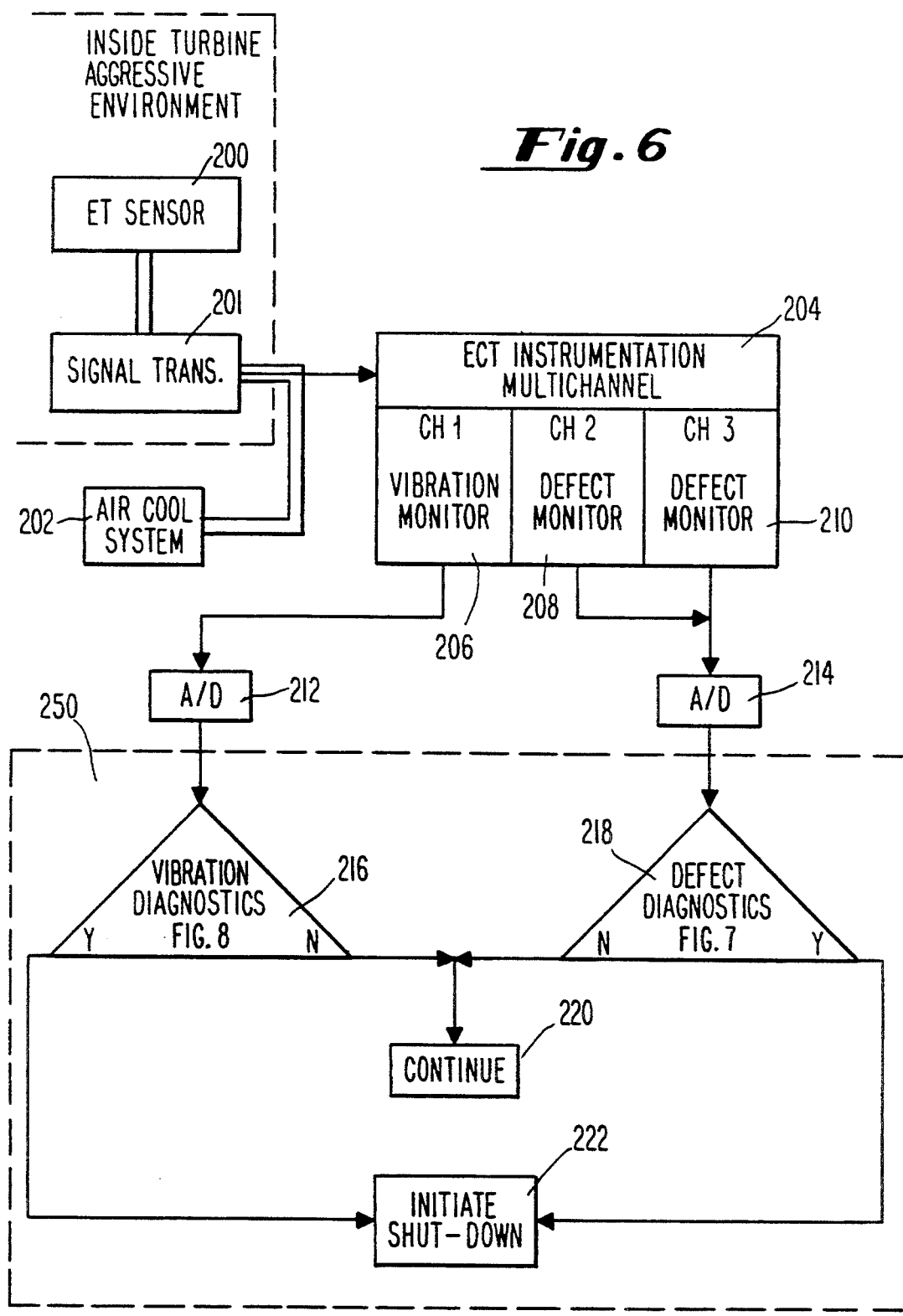
FIG. 6 is a system block diagram of the eddy current sensing system according to a preferred embodiment of the present invention.

A block diagram of an eddy current sensing system according to the present invention is shown in FIG. 6. Preferably, the system utilizes the eddy current sensor described herein. However, it should be understood that other eddy current sensors may be used in the system shown in FIG. 6. The eddy currents sensed by the pickup coils of eddy current sensor 200 are provided as an output using suitable signal cable 201. Thus the signal carried on the signal cable 201 has a magnitude related to the eddy current detected in the pickup coils.

The ECT (Eddy Current Testing) instrument 204 receives an input from the signal cable 201. The ECT instrument 204 is preferably a multichannel device such that each channel can be separately configured based upon the intended application, the dynamics of the rotating member to be monitored, the conditions to be monitored, and a number of other possible factors. Such an ECT instrument is commercially available from Zetec Inc., Rohman Inc., Nortec Inc., and Foerster Inc. If the eddy current sensor shown in FIGS. 3A and 3B is used as eddy current sensor 200 in a combustion turbine engine for monitoring crack formation in an air separator and displacement of the row 1 disc, the ECT instrument 204 is preferably configured for three channels. The first channel shown as channel 1 at 206 is used for detecting displacement. Channels 2 and 3 at 208 and 210, respectively, are used for detecting crack formation on the surface of the rotating member being monitored. In this preferred embodiment, channel 2 corresponds to the first coil sensor 100 and channel 3 corresponds to the second coil sensor 101. However, it should be understood that any number of coil sensors may be used depending on the specific requirements for the sensor's intended use.

If it is assumed that the eddy current sensing system is to be used in a combustion turbine engine to detect crack formation in an air separator and displacement of the row 1 disc, as shown in FIGS. 1 and 2, the ECT instrument channels can be defined by calculable frequencies. For instance, consider the formation of a crack on the surface of the air separator. The air separator is approximately 52 inches in diameter and rotates at a speed of about 3600 rpm (60 revolutions per second). Thus the surface of the air separator travels past the eddy current sensor at a rate of approximately 250 meters per second (9800 inches per second: $52\pi$ inches in perimeter multiplied by 60 revolutions per second). If the probe field has a detection window of approximately 1.3 cm (½ inch) in length, (e.g. using the u-shaped coil shield shown in FIG. 5A), then it would take about 50 μsec for 1.3 cm (½ inch) of the rotating surface to travel from the beginning of the probe's detection window to the end of the probe's detection window. Thus any crack detected in the probe field would in this particular application have a characteristic frequency of 20 KHz (the reciprocal of 50 μsec.). In such a case, a 20 KHz bandpass filter is selected from the ECT instrument selectable filter parameters for channels 2 and 3. The characteristic frequency for detecting displacement or vibration of the row 1 disc, is preferably 60 Hz. It should be understood that a similar analysis would be performed to determine the characteristic frequency of each condition to be monitored. A bandpass filter having a center frequency of about 60 Hz or even a lowpass filter having a cutoff frequency around 60 Hz would be selected from the ECT instrument's selectable filter parameters for channel 1.

The output of the ECT instrument 204 is one or more filtered analog signals, where the number of outputs corresponds to the number of channels used by the ECT instrument 204. Analog-to-digital converters 212 and 214 convert the analog output of the ECT instrument 204 to a digital signal input to an appropriate processor 250. In a preferred embodiment, the digital signals associated with channels 2 and 3 are analyzed by a defect diagnostic system 218 implemented by processor 250. Similarly, the digital signal associated with channel 1 is analyzed by the displacement diagnostic system 216. As long as no defects or displacements conditions are detected, the system continues as shown at 220 monitoring these conditions. However, if a critical defect or displacement is discovered, the system can be manually shut down or automatically shut down under software control as shown at 222.

Figure 7:
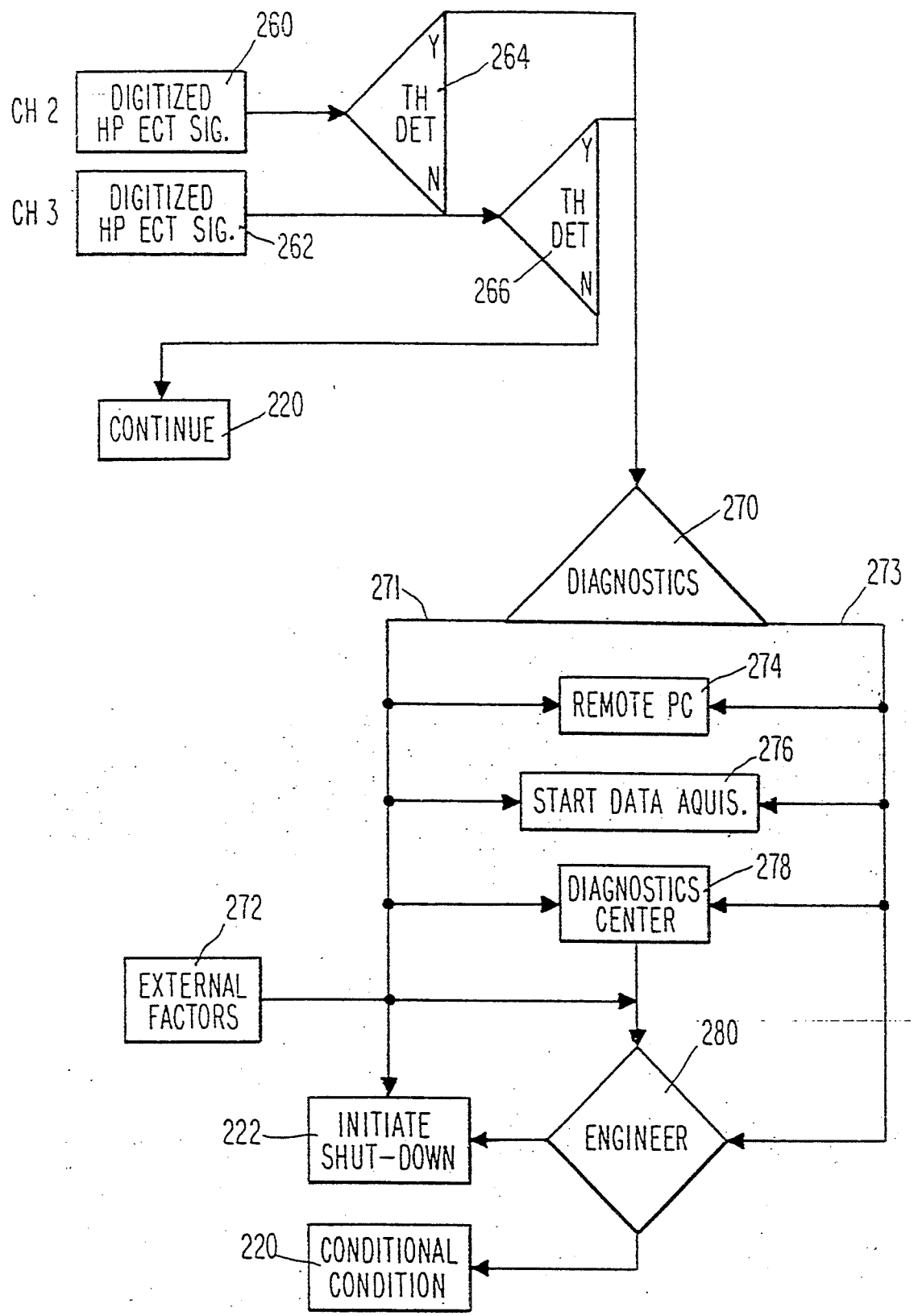
FIG. 7 is a block diagram of the defect diagnostic system according to a preferred embodiment of the present invention.

FIG. 7 is a block diagram of the diagnostic system 218 for monitoring defects in the surface of a rotating member, such as the air separator in a combustion turbine according to a preferred embodiment of the invention. The digital inputs 260 and 262 associated with channel 2 and 3 of the ECT instrument, respectively, are provided as respective inputs to threshold detectors 264 and 266. Threshold detectors 264 and 266 compare the magnitude of the digital inputs 260 and 262 with a predetermined threshold. A possible defect is detected when one or both of the filtered outputs exceed the threshold. Thus, the threshold level is based upon a number of factors, (e.g. the signal-to-noise ratio of the digital inputs 260 and 262), but it should be selected to balance a maximum probability of detection with a minimum probability of false alarm as is well known.

To maximize the probability of detection, the sampling rate of the pickup coils should also be maximized. The output of the pickup coils can be effectively sampled at a rate equal to the frequency of the alternating current driving the driver coil of the eddy current sensor. Therefore, it is preferable to use an alternating current having the highest possible frequency. For instance, if the eddy current sensor used in the combustion turbine engine described above has an operating frequency of 200 KHz, it would be possible to monitor the surface of the air separator every 5 μsec. or about every 1.2 μm (0.05 inches: 9800 inches per second multiplied by 5 μsec.). Depending upon the particular application, it may be necessary to increase the operating frequency to 1 MHz to achieve the desired sensitivity (approximately 0.01 inches).

As long as the predetermined threshold has not been exceeded, monitoring continues at 220. However, if a defect is detected by either threshold detector 264 or 266, an assessment means 270 which is preferably diagnostic software further analyzes the filtered outputs which exceed the threshold as determined by threshold detectors 264 and 266. For instance, when a crack forms on the surface of a rotating member it may not be critical to the operation of the combustion turbine engine. More specifically, if the crack grows to a certain length, it may require that the combustion turbine engine be shut down for safety reasons or for replacement of the defective part or parts. Alternatively, the size of the defect may not be deemed critical, but the crack's growth rate may be so rapid that it requires the combustion turbine engine to be shut down. By utilizing at least two channels to monitor a defect, it should be understood that both the size of the condition, a crack in this example, and its growth rate can be determined by analyzing the time and occurrences when the filtered outputs exceed the predetermined threshold. Thus, the assessment means 270 may determine the length or the growth rate of a crack and compare that data to predetermined standards based on conditions requiring the combustion turbine engine to be shut down.

For instance, suppose coil sensors 100 and 101 shown in FIG. 3A are disposed above the rotating surface at about 5 cm (2 inches) and 10 cm (4 inches) from the edge of the rotating surface where a crack may be expected to begin as shown in FIG. 4. Also for exemplary purposes, assume that it is determined that a crack greater than about 10 cm (4 inches) in length is a critical condition. Then if a crack is detected by threshold detector 266, the condition will be defined as critical since the crack would be determined to be at least 10 cm (4 inches) in length. Alternatively, assume a crack with a growth rate greater than about 5 cm per hour (2 inches per hour) is determined to be a critical condition. Then if the crack is first detected by threshold detector 264 and then detected by threshold detector 266 within the next two hours, the condition would again be defined as critical because the crack growth rate would be greater than or equal to 5 cm per hour (2 inches per hour).

After the assessment means 270 makes a determination that the condition is critical, the defect diagnostic system preferably initiates an automatic shut down procedure 222. In a more preferred embodiment, a manual override is provided so that the condition may be monitored by personnel before the combustion turbine is powered down. For instance, a remote personal computer (PC) 274 is provided so that a trained technician or engineer may evaluate the data to determine whether or not the shut down procedure 222 should be initiated. The remote PC 274 receives an input 271 from the assessment means 270 providing an indication of whether the condition has been determined to be critical or routine. In a preferred embodiment, the assessment means 270 also provides an output of data 273 representing the filtered signal characteristics and other data generated by the diagnostic software, e.g., the current size of the defect, the current growth rate, etc. In a further preferred embodiment, external factors 272 such as vibrational data, temperature changes, fuel considerations, or any other factor potentially affecting the condition being monitored may be provided as an input to the remote PC 274 from appropriate external sources.

In another preferred embodiment, one or more engineers 280 may monitor the operation of the combustion turbine engine from a remote diagnostic center 278. In this preferred embodiment, an alarm may be sounded at the diagnostic center 278 when a critical condition is detected. A diagnostic PC 276 provided at the diagnostic center 278 preferably begins acquiring the data 273 after the assessment means 270 has analyzed the outputs from the threshold detectors 264 and 266. If the condition is determined to be routine, the engineer 280 preferably has the option to initiate the shut down procedure 222. Similarly, if the condition has been determined to be critical, the engineer 280 preferably has the option to decide to continue the operation conditionally as shown at 220 depending upon the data 273.

Figure 8:
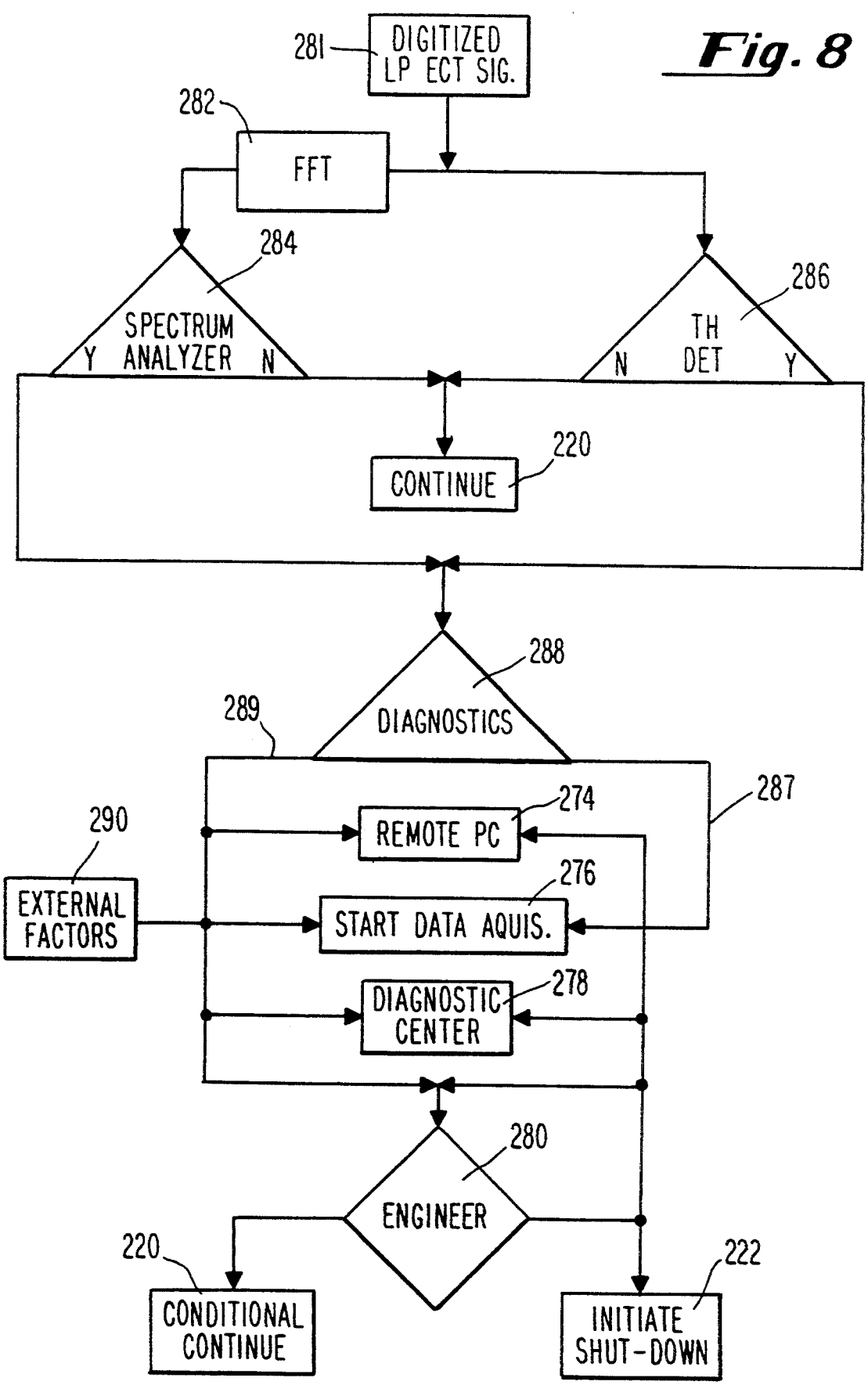
FIG. 8 is a block diagram of the displacement diagnostic system according to a preferred embodiment of the present invention.

FIG. 8 is a block diagram of a preferred embodiment of the diagnostic system for monitoring a displacement of a rotating member. The digitized input signal 281 associated with channel 1 of the ECT instrument 204 is provided as an input to threshold detector 286. Threshold detector 286 essentially serves to detect when the signal 281 exceeds a predetermined threshold as described above in conjunction with threshold detectors 264 and 266. In a more preferred embodiment, an FFT (Fast Fourier Transform) 282 is performed on the digital input signal 281 and analyzed by spectrum analyzer 284. Spectrum analysis may be useful in determining the characteristics of the displacement so that, for instance, the cause of the displacement may be ascertained from the data generated by the FFT 282.

If no displacement has been detected by either the threshold detector 286 or by the spectrum analyzer 284, the monitoring continues at 220. If displacement has been detected, then the data must be analyzed further to determine the severity of the displacement. The assessment means 288 analyzes the data from the threshold detector 286 and the spectrum analyzer 284, if one is used, to determine whether the displacement is critical or routine.

As described above it may be preferable, depending upon the particular application, to provide a remote PC 274, a diagnostic PC 276 in a diagnostic center 278, or both, so that trained personnel may independently evaluate the data 289 output from the assessment means 288. It is also preferred to provide an external factors interface 290 so that additional data provided by appropriate external sources can be considered where that data may have some effect on the displacement data 289.

While the invention has been described and illustrated with reference to specific embodiments, those skilled in the art will recognize that modification and variations may be made without departing from the principles of the invention as described hereinabove and set forth in the following claims.

We claim:

1. An eddy current sensing system comprising:
    an eddy current sensor disposed in an enclosed environment of a rotating member, said eddy current sensor having at least one driver coil for inducing an eddy current in said rotating member and having at least one pickup coil for sensing said eddy current induced in said rotating member, said pickup coil providing an output indicative of said eddy current so sensed;
    an eddy current testing instrument coupled to said at least one pickup coil for filtering said output from said at least one pickup coil and for providing at least one filtered output, each filtered output being related to a condition of said rotating member to be monitored;
    a threshold detector coupled to said eddy current testing instrument for receiving each said filtered output and detecting occurrences when any of said filtered outputs exceed a predetermined threshold relating to said condition, said threshold detector providing an output indicative of each occurrence so detected;
    an assessment meads coupled to said threshold detector receiving said output from said threshold detector, and an input related to external factors affecting said analysis of said condition; and
    analyzing said output indicative of each said occurrence to determine a severity of said condition.

2. The system of claim 1, wherein said condition to be monitored is a defect on a surface of said rotating member.

3. The system of claim 1, wherein said condition to be monitored is a displacement of said rotating member.

4. The system of claim 1, wherein said eddy current sensor is operational at temperatures above 165° C. (330° F.).

5. The system of claim 1, wherein said rotating member is part of a combustion turbine engine, said system providing substantially real time monitoring of said condition while said combustion turbine is operating.

6. The system of claim 1, wherein said eddy current sensor further comprises:
    a second pickup coil for sensing said eddy current induced in said rotating member, said pickup coils being configured differentially to provide a single output indicative of said eddy current so sensed, said single output being coupled to an input of said eddy current test instrument.

7. The system of claim 1, wherein said driver coil in combination with said pickup coil defines a first coil sensor, the system further comprising:
    at least a second coil sensor having one said driver coil and said at least one pickup coil, said coil sensors being positioned in series such that each coil sensor provides an output to said eddy current testing instrument, said eddy current testing instrument providing a separate filtered output corresponding to each of said coil sensors, said assessment system receiving an input of each filtered output and evaluating said filtered outputs to determine a progression of said condition.

8. A method for in-situ monitoring of a rotating member utilizing an eddy current sensing system, comprising the steps of:
    inducing an eddy current in said rotating member;
    detecting said eddy current so induced;
    providing a signal indicative of said eddy current so detected and defining the same as a detected signal;
    filtering said detected signal to produce a filtered signal, said filtered signal being indicative of a condition of said rotating member to be monitored;
    identifying occurrences in which a magnitude of said filtered signal exceeds a predetermined threshold;
    analyzing, upon said identification, said filtered signal to determine whether said condition exists in said rotating member;
    determining the severity of said condition if said condition exists; and
    initiating a shut down of said combustion turbine engine based upon said determination.

9. The method of claim 8, wherein said condition to be monitored is a crack formation in said rotating member.

10. The method of claim 8, wherein said condition to be monitored is a displacement of said rotating member.

11. The method of claim 8, wherein said rotating member is part of a combustion turbine engine.

12. The method of claim 8, further comprising the steps of:
   determining the severity of said condition if said condition exists; and
   triggering an alarm at a remote diagnostic center based upon said determination.

13. The method of claim 11, wherein access to data indicative of said filtered signal is available at a computer remote from said combustion turbine engine, further comprising the steps of:
   determining the severity of said condition if said condition exists; and
   monitoring said condition from said remote computer by evaluating said data.

14. The method of claim 8, further comprising the step of:
   analyzing, upon a determination that said condition exists, a progression of said condition.

* * * * *